US011391746B2

(12) United States Patent
Garnier et al.

(10) Patent No.: US 11,391,746 B2
(45) Date of Patent: Jul. 19, 2022

(54) TESTING DEVICE FOR IDENTIFYING ANTIGENS AND ANTIBODIES IN BIOFLUIDS

(71) Applicant: Monash University, Victoria (AU)

(72) Inventors: Gil Garnier, Victoria (AU); Wei Shen, Victoria (AU); Mohidus Samad Khan, Victoria (AU); Xu Li, Victoria (AU); George Thouas, Victoria (AU)

(73) Assignee: MONASH UNIVERSITY, Clayton (AU)

( * ) Notice: Subject to any disclaimer, the term of this patent is extended or adjusted under 35 U.S.C. 154(b) by 234 days.

(21) Appl. No.: 15/175,477

(22) Filed: Jun. 7, 2016

(65) Prior Publication Data
US 2016/0291039 A1 Oct. 6, 2016

Related U.S. Application Data

(62) Division of application No. 13/497,704, filed as application No. PCT/AU2010/001255 on Sep. 24, 2010, now abandoned.

(30) Foreign Application Priority Data

Sep. 24, 2009 (AU) ............... 2009904643

(51) Int. Cl.
*G01N 33/80* (2006.01)
*G01N 33/558* (2006.01)
*G01N 30/90* (2006.01)
*G01N 21/82* (2006.01)
*G01N 21/75* (2006.01)

(52) U.S. Cl.
CPC ............. *G01N 33/80* (2013.01); *G01N 21/82* (2013.01); *G01N 30/90* (2013.01); *G01N 33/558* (2013.01); *G01N 2021/752* (2013.01); *G01N 2021/757* (2013.01); *G01N 2021/825* (2013.01)

(58) Field of Classification Search
None
See application file for complete search history.

(56) References Cited

U.S. PATENT DOCUMENTS

| | | | | |
|---|---|---|---|---|
| 4,943,522 A * | 7/1990 | Eisinger | ............... | G01N 33/558 436/514 |
| 5,145,789 A | 9/1992 | Corti et al. | | |
| 5,164,598 A * | 11/1992 | Hillman | ............... | B01F 5/0618 250/341.3 |
| 5,585,278 A * | 12/1996 | Vunnam | ........... | G01N 33/54346 436/518 |
| 5,904,824 A | 5/1999 | Oh | | |
| 10,758,846 B2 * | 9/2020 | Mace | ............... | G01N 33/57415 |
| 2002/0172937 A1 * | 11/2002 | Dave | ............... | G01N 33/56905 435/5 |
| 2006/0018797 A1 | 1/2006 | Burnell et al. | | |
| 2006/0194342 A1 * | 8/2006 | Bond | ............... | G01N 33/5304 436/518 |
| 2008/0241962 A1 | 10/2008 | Wang | | |
| 2008/0248504 A1 * | 10/2008 | Ruddell | ............... | G01N 33/558 435/7.25 |
| 2009/0035743 A1 * | 2/2009 | Minter | ............... | G01N 33/80 435/2 |
| 2010/0062414 A1 | 3/2010 | Yamamoto et al. | | |
| 2010/0267065 A1 * | 10/2010 | Geiger | ............... | C12Q 1/56 435/13 |
| 2012/0322086 A1 * | 12/2012 | Garnier | ............... | G01N 30/90 435/7.25 |
| 2015/0323525 A1 * | 11/2015 | Vidarsson | ............... | G01N 33/80 506/9 |

FOREIGN PATENT DOCUMENTS

| | | |
|---|---|---|
| EP | 0223978 B1 | 8/1992 |
| WO | WO 1987/007304 | 12/1987 |
| WO | WO 2005/073733 | 8/2005 |
| WO | WO 2005/098439 | 10/2005 |
| WO | WO 2006/074665 A2 | 7/2006 |
| WO | WO 2008/083687 | 7/2008 |
| WO | WO 2010/003188 | 1/2010 |
| WO | WO 2011/000047 | 1/2011 |
| WO | WO 2011/035385 | 3/2011 |

OTHER PUBLICATIONS

Anderson, "Analytical Techniques for Cell Fractions. XVIII. Use of Cellulose Wicks to Monitor Agglutination Reactions", Analytical Biochemistry, Mar. 1970, 38, 175-189.
Carrilho et al., "Understanding Wax Printing: A Simple Micropatterning Process for Paper-Based Microfluidics", Analytical Chemistry, Aug. 15, 2009, 81, 7091-7095.
Martinez et al., "Three-Dimensional Microfluidic Devices Fabricated in Layered Paper and Tape", PNAS, Dec. 16, 2008, vol. 105, No. 50, 19606-19611.
Li et al., "Paper-Based Microfluidic Devices by Plasma Treatment", Analytical Chemistry, Dec. 1, 2008, 80, 9131-9134.
Pelton et al., "Bioactive paper provides a low-cost platform for diagnostics", Trends in Analytical Chemistry, Sep. 2009, vol. 28, Issue 8, 925-942.

\* cited by examiner

*Primary Examiner* — Ann Montgomery
(74) *Attorney, Agent, or Firm* — BakerHostetler (57) ABSTRACT

A testing device for identifying an antigen or antibody within a biofluid sample including: a substrate having a hydrophilic surface thereon; the surface including a collection zone, and at least one detection zone extending therefrom; wherein the biofluid sample can be mixed with a specific antigen or antibody, and deposited on the collection zone and transferred by capillary action to the detection zone; the antigen or antibody in the biofluid sample reacting with an appropriate said antibody or antigen thereby resulting in a visual indication within the detection zone.

4 Claims, 7 Drawing Sheets

| Time, t (min) | AB+ Blood wicking on Anti-A (1.0x) active paper |
|---|---|
| 0.0 | |
| 1.0 | |
| 2.0 | |
| 3.0 | |
| 4.0 | |
| 5.0 | |

(a) Paper based (ABO) blood type detection device

(b) Detection of AB+ blood

(c) Detection of AB- blood

(d) Detection of A+ blood

(e) Detection of A- blood

(f) Detection of B+ blood (g) Detection of B- blood (h) Detection of O+ blood (i) Detection of O- blood

Figure 8

TESTING DEVICE FOR IDENTIFYING ANTIGENS AND ANTIBODIES IN BIOFLUIDS

CROSS REFERENCE TO RELATED APPLICATIONS

This application is a Divisional of U.S. patent application Ser. No. 13/497,704 filed May 31, 2012, which is the National Stage of International Application No. PCT/AU2010/001255, filed Sep. 24, 2010, which claims the benefit of Australian Application No. 2009904643 filed Sep. 24, 2009, the disclosures of which are incorporated herein by reference in their entireties.

TECHNICAL FIELD

The present invention is directed to the identification of antigens and antibodies within a biofluid. While the invention will be described with specific reference to its use in determining a person's blood type, it is to be appreciated that other applications of the invention are also envisaged.

BACKGROUND

Blood is essential for sustaining living tissue, with the most important roles of supplying oxygen and other soluble nutrients, immune protection and metabolic turnover. While it is a tissue in its own right, blood in a chemical sense can be considered as a stable, highly packed colloid suspension made of red blood cells (erythrocytes, 4-6 million/mL, 6-8 µm), white cells (leukocytes, 4000-6000/mL, 10-21 µm), platelets (150,000-400,000/mL, 2-5 µm) carried within a fluid solution (serum) containing a host of biomolecules (eg albumins, fatty acids, hormones), metabolites and electrolytes. A subset of these biomolecules, such as the binding proteins responsible for tissue immunity (antigens) and blood type, are directly adsorbed onto the surface of blood cells. Common portable testing methods for blood include analysis of glucose content, cholesterol, metabolic panel (sodium, potassium, bicarbonate, blood urea nitrogen, magnesium, creatine, calcium, triglycerides), microbial and disease markers and protein molecular profile (liver, prostate). Surprisingly, and in spite of its vital importance, there are no convenient low cost disposable tests available for "on the spot" analysis of blood type. Blood samples are typically outsourced to an analytical laboratory. Reliable low cost tests which are able to instantaneously and reliably provide critical blood analysis without the requirement of sophisticated laboratory analytical instrumentation such as chromatographic and spectroscopic methods, would be invaluable for improving human health in developing countries, where economic resources are limited. Blood analysis is also important in non-human applications, such as veterinary medicine, where there is a demand for low cost and versatile devices suitable for field use.

SUMMARY

With this in mind, according to one aspect of the present invention, there is provided a testing device for identifying an antigen or antibody within a biofluid sample including;
a substrate having a hydrophilic surface thereon;
the surface including a collection zone, and at least one detection zone extending therefrom;
wherein the biofluid sample can be mixed with a specific antigen or antibody, and deposited on the collection zone and transferred by capillary action to the detection zone;
the antigen or antibody in the biofluid sample reacting with an appropriate said antibody or antigen thereby resulting in a visual indication within the detection zone.

According to another aspect of the present invention there is provided a testing device for identifying an antigen or antibody within a biofluid sample including;
a substrate having a hydrophilic surface thereon;
the surface including a collection zone, and at least one detection zone extending therefrom;
the detection zone having an antibody or antigen immobilised therein;
wherein the biofluid sample can be deposited on the collection zone and transferred by capillary action to the detection zone;
the antigen or antibody in the biofluid sample reacting with an appropriate said antibody or antigen within the detection zone thereby resulting in a visual indication therein.

The substrate may be formed from paper or other cellulosic materials. Alternatively, the substrate may include a chromographic layer thereon or may be a wettable porous medium.

The biofluid sample being tested may preferably be blood, and the visual indication may be due to an agglutination of the blood upon reaction with a specific antibody resulting in reduced wicking and/or separation of the blood in the detection zone.

The substrate surface may have a hydrophilic microfluidic channel pattern thereon defining the collection zone and the detection zone. Preferably, a plurality of detection zones may extend from the collection zone.

It has been found that red blood cell agglutination, triggered by specific antigen interaction, drastically decreases blood wicking and dispersion on paper or chromatographic media. The agglutination process also considerably enhances the chromatographic separation (elution) of the individual blood components, especially the red blood cells from the serum. The testing device according to the present invention can allow direct analysis of blood cells because of this visual indication. This can be performed instantaneously, either with a detection/reporting system built-in to the device or in conjunction with other off-line analytical equipment. The testing device may also allow for the identification and quantification of specific biomolecules (eg antigens and antibodies) based on induced coagulation, followed by the wicking and elution (separation) of the soluble protein fraction from the blood sample onto the porous substrate. The blood colloids, whose coagulation directly affects their wicking/separation, can either be present in the fluid of interest, such as the red blood cells of blood, or introduced as nanoparticles (gold, silver, micro-silica, zeolite, titanium dioxide and the like). In the latter case, the nanoparticle is typically covered with the specific counter-biomolecule or molecule of interest used as sensitive reporter component. The colloid particles may be of a size ranging from 1 nm to 100 µm and may be introduced into the biofluid being analysed.

In the application of the present invention for determining the type of blood group, the present invention may determine the antigens present within a blood sample, the antigens determining whether the blood type is type A, B, O, AB and Rhesus +/−. Antibodies A, B and D (Rhesus) are deposited into separate detection zones. It may also be preferable to include an untreated control zone in one of the detection zones. A drop of blood is then deposited on the central collection zone, the blood sample being transferred by capillary action to each of the detection zones. When the blood sample contacts an appropriate antibody, the reaction of the red blood cells antigen with its corresponding antibody results in agglutination or coagulation of the red cells. This agglutination results in a drop in velocity of the movement of the blood sample along the microfluidic channel providing the detection zone and separation of the red blood cells from the serum. The velocity of the blood samples travelling along other detection zones with non-specific antibodies is unaffected. This visual contrast facilitates easy and rapid identification of the blood type of the blood sample.

The applicant has developed a low cost paper based microfluidic system which is described in International patent application no. PCT/AU2009/000889 details of which are incorporated herein by reference. The microfluidic systems described in this application utilise a paper based substrate, with the described fabrication methods producing hydrophilic microfluidic channels on the paper based substrates. It should be noted that the term paper is used in this application to refer to all cellulosic materials including woven fabrics and non-woven cellulosic material as well as paper. The microfluidic systems described in these applications can be readily adapted for the purpose of the present invention.

The testing device according to the present invention may also be used to detect illness as a result of blood cell malfunction on the blood cells being of abnormal shape as is the case with malaria. Alternatively, the testing device according to the present invention may be used to detect illness by identifying the presence of an antigen, antibody, virus (such as HIV, influenza) or protein.

In the International application, the microfluidic channels are fabricated by printing a hydrophobic agent on the substrate surface to define a peripheral edge of the microfluidic channels. According to the present invention, the antibody or antigen may also be printed within the microfluidic channels. The technology used, namely ink jet printing technology, may also be used to print the antigen or antibody within the microfluidic channels.

According to a further aspect of the present invention, there is provided a method for identifying an antigen or antibody within a biofluid sample, including:

mixing the biofluid sample with a specific antigen or antibody, depositing the mixed biofluid sample on a collection zone of a testing device including a substrate having a hydrophilic surface thereon, the surface including said collection zone and at least one detection zone extending therefrom, the biofluid sample being transferred by capillary action to the detection zone; and identifying the antigen or antibody by a resultant visual indication within the detection zone arising where the antigen or antibody in the biofluid sample reacts with an appropriate said antibody or antigen.

According to yet another aspect of the present invention, there is provided a method for identifying an antigen or antibody within a biofluid sample, including:

depositing the biofluid sample on a collection zone of a testing device including a substrate having a hydrophilic surface thereon, the surface including said collection zone and at least one detection zone extending therefrom, the detection zone having an antibody or antigen immobilised therein, the biofluid sample being transferred by capillary action to the detection zone; and identifying the antigen or antibody by a resultant visual indication arising where the antigen or antibody in the biofluid sample reacts with an appropriate said antibody or antigen within the detection zone.

BRIEF DESCRIPTION OF THE DRAWINGS

It will be convenient to further describe the invention with respect to the accompanying drawings which illustrate preferred embodiments of the testing device according to the present invention. Other embodiments of the invention are possible, and consequently, the particularity of the accompanying drawings is not to be understood as superseding the preceding description of the invention.

In the drawings:

FIG. 6 A-F shows the operation of a testing device according to the present invention incorporating valves and switches;

DETAILED DESCRIPTION OF ILLUSTRATIVE EMBODIMENTS

The applicants have discovered that blood agglutination mediated by specific antibody-antigen interactions drastically affects its separation behaviour on contact with paper or any thin layer chromatographic surface. The invention relies on this biochemical phenomenon to control the rate of wicking and separation, which enables (i) identification and quantitative assessment of a specific antibody/antigen, (ii) blood typing, and potentially (iii) identification of blood-borne pathogens as a disease diagnostic. The present invention is intended predominantly for applications in human and veterinary medicine and biotechnology.

Standard techniques for detection of blood agglutination are traditionally manual, involve dispensing of antibodies on a glass slide and microscopic visualization. However, the visualisation of agglutination is often subjective, and its automation requires a bank of sophisticated analytical equipment. The present invention provides a single-step blood test that simplifies and circumvents these difficulties.

One application of the invention involves a two step process in which the blood sample is first coagulated/agglutinated by combining it with the specific antibody/antigen of interest, followed by its deposition on the analytical substrate (eg Non-woven paper or porous mesh) on which the sample wicking and separation by elution/chromatography is measured, directly or indirectly. These two mixing steps can be enhanced and more accurately performed by mixing on paper substrates using built-in valving and channelling control features.

A second application of the invention involves a single-step process in which the biofluid/sample is deposited directly on the substrate/device which has previously been treated with the specific antigen/antibody. For this process, the analyte samples simultaneously coagulate and elude on the same substrate. The measured elution velocity and the extent of sample separation are directly related to the extent of coagulation, enabling the concentration of the biomolecule to be detected and quantified at the same time.

Both applications of the invention can be applied to a test device made of paper or any non-woven chromatographic surface, which are relatively cost effective. These substrates are also able to be modified with the use of advanced printing techniques to create microfluidic features composed of hydrophobic materials, as previously described in the applicant's International application no. PCT/AU2009/000889. Combined with methods of direct antibody deposition using printing, manufacture and placement of antibody reagent can enable very accurate spatial control of blood flow within the paper substrate.

EXAMPLES

Example 1

Sequential Agglutination/Coagulation of Blood Followed by Wicking on Paper: B+ (two step process) (See FIG. 1)

Figure 1:
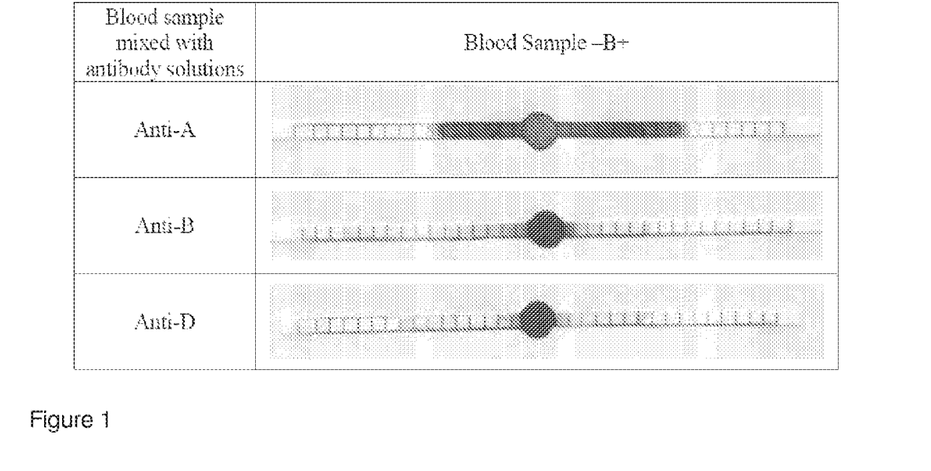
FIG. 1 shows a testing device according to the present invention used to determine B+ blood.

Antibody A and B (Epiclone™ Anti-A, Anti-B, and Anti-D; CSL, Australia) solutions were used. Anti-A and Anti-B come as blue and yellow colour reagents, respectively. 'B+' blood was used in this study. The blood sample was supplied into plastic vials with anti-coagulant. 'B+' blood was separately mixed with pure Anti-A and Anti-B (as received) to prepare 100 µL solution. Paper strips (70 mm×2 mm) were made from Whatman #4 filter paper on which 2 mm unit marks were printed. The paper strips were soaked into phosphate buffer saline (PBS). Excess PBS was removed from the paper strips using standard blotting papers (Drink Coster Blotting, 280 GSM). The paper strips were then placed on Reflex Paper (80 GSM). 20 µL of every mixed solution was dispensed at the centre of paper strip using a calibrated micro-pipette. Pictures were taken after 4 minutes wicking.

It can be seen that:

B+ blood mixed with the solution of antibody A wicked and did not separate upon mixing and paper elution/wicking.

B+ blood mixed with the solution of antibody B wicked and STRONGLY separated (red cells from serum) and showed wicking.

B+ blood mixed with the solution of antibody D (Rhesus +) wicked and STRONGLY separated (red cells from serum).

A blood sample agglutinated/coagulated upon contact with its specific antibodies separated/eluded upon contact with paper (here Blood B+ with Anti-B and Anti-D antibodies).

A blood sample upon contact with non-specific antibody (here Blood B+ with Anti-A) does not agglutinate and does not separate/elute upon contact with paper.

This dramatic difference in elution/separation of blood/antibody mixing can be used to communicate specific agglutination and therefore can be used to identify blood typing.

Example 2

Sequential Agglutination/Coagulation of Blood Followed by Wicking on Paper: O+ (two step process) (See FIG. 2)

Figure 2:
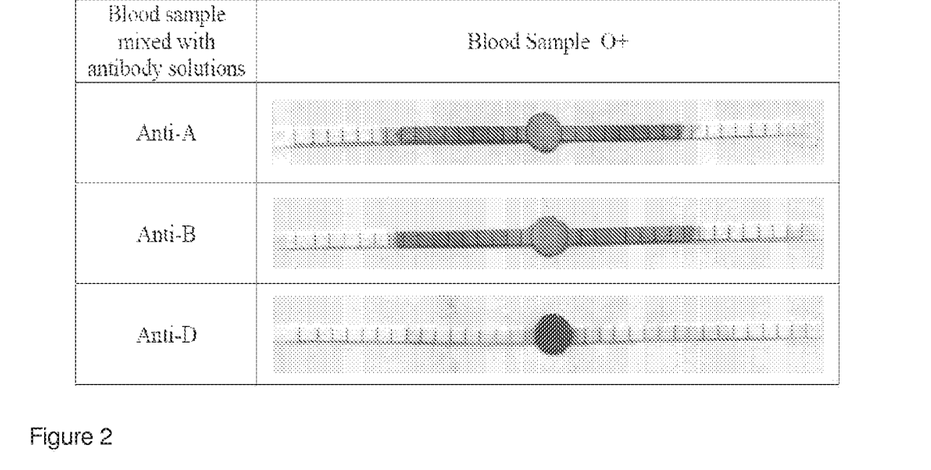
FIG. 2 shows a testing device according to the present invention used to determine O+ blood.

Antibody A and B (Epiclone™ Anti-A, Anti-B and Anti-D; CSL, Australia) solutions were used. Anti-A and Anti-B come as blue and yellow colour reagents, respectively. 'O+' blood was used in this study. The blood sample was supplied into plastic vials with anti-coagulant. 'O+' blood was separately mixed with Anti-A and Anti-B to prepare 100 µL solution. Paper strips (70 mm×2 mm) were made from Whatman #4 filter paper on which 2 mm unit marks were printed. The paper strips were soaked into phosphate buffer saline (PBS). Excess PBS was removed from the paper strips using standard blotting papers (Drink Coster Blotting, 280 GSM). The paper strips were then placed on Reflex Paper (80 GSM). 20 µL of every mixed solution was dispensed at the centre of paper strip using a calibrated micro-pipette. Pictures were taken after 4 minutes wicking.

It can be seen that:

O+ blood mixed with the solution of antibody A wicked and did not separate upon mixing and paper elution/wicking.

O+ blood mixed with the solution of antibody B wicked and did not separate (red cells from serum) and showed wicking.

O+ blood mixed with the solution of antibody D (Rhesus +) wicked and STRONGLY separated (red cells from serum).

A blood sample agglutinated/coagulated upon contact with its specific antibodies separated/eluded upon contact with paper (here Blood O+ with Anti-D antibodies).

A blood sample upon contact with non-specific antibody (here Blood O+ with Anti-A and Anti-B) does not agglutinate and does not separate/elute upon contact with paper.

This dramatic difference in elution/separation of blood/antibody mixing can be used to communicate specific agglutination and therefore can be used to identify blood typing.

Example 3

Simultaneous Agglutination/Coagulation of Blood Followed by Wicking on Paper: Effect of antigen concentration (one step process) (See FIG. 3)

Figure 3:
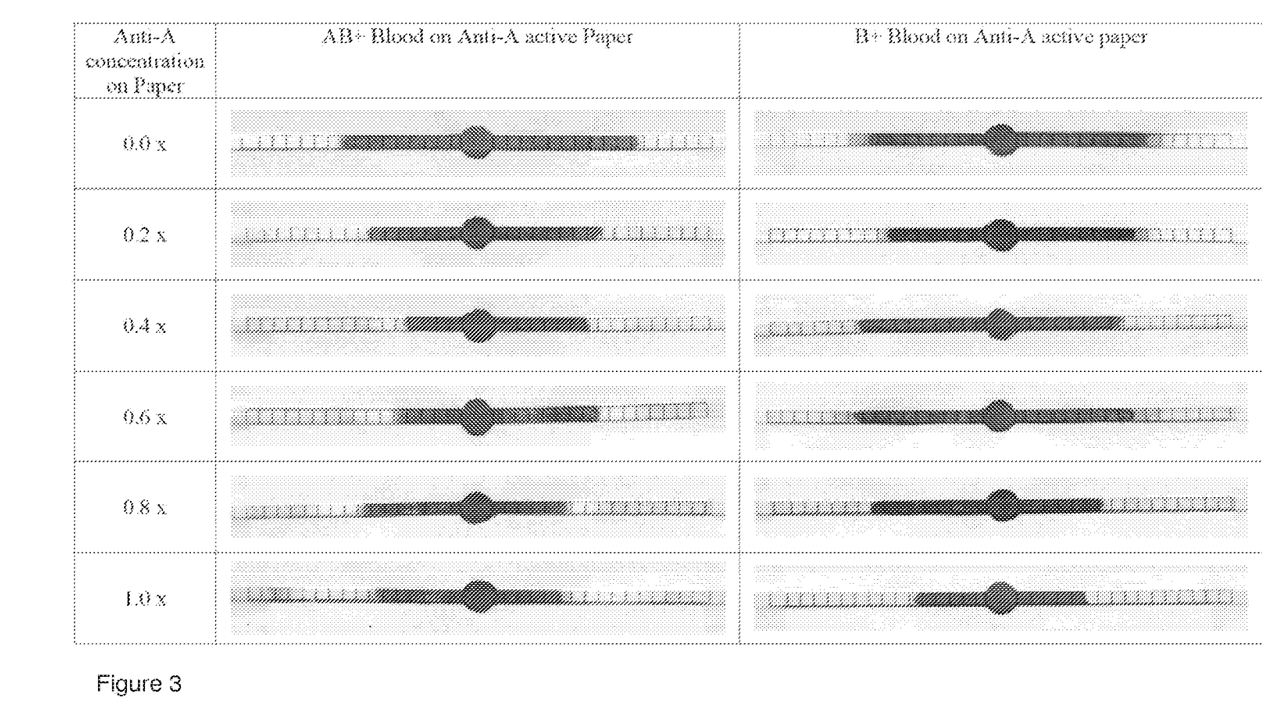
FIG. 3 shows the testing device according to the present invention using AB+ and B+ blood.

In another embodiment of the invention, the paper is first treated with specific antibodies, dried or conditioned before been exposed to a sample of pure blood. This example provides a single step treatment in which the only requirement is to deposit a drop of blood on the paper. This example also illustrates the effect of diluting the antibody solution on the wicking and separation performance of blood on paper. Antibody dilution affects the ratio blood (with its antigen) antibody.

Antibody A and B (Epiclone™ Anti-A and Anti-B; CSL, Australia) solutions were used. Anti-A and Anti-B come as blue and yellow colour reagents, respectively. "AB+" and 'B+' blood were used in this study. The blood sample was supplied into plastic vials with anti-coagulant. Paper strips (70 mm×2 mm) were made from Whatman #4 filter paper on which 2 mm unit marks were printed. Paper strips were soaked into antibody solutions of different concentrations (Anti-A@1.0×, 0.8×, 0.6×, 0.4×, 0.2× and 0.0×); phosphate buffer saline (PBS) was used as diluent. Excess antibody was removed from the paper strips with blotting papers. The antibody (Anti-A) active paper strips were then placed on Reflex Paper. Blood drops of 20 µL were dispensed at the centre of paper strip using a calibrated micro-pipette. The wicking distance was measured from centre to either direction. Pictures were taken after 10 minutes.

The results are shown in FIG. 3. It can be seen that:

Blood separates upon wicking with its specific antibody treated paper.

Blood separation is a non-linear function of the antibody concentration on the treated paper. The higher the antibody concentration, the more abrupt is the cell separation from the serum.

There is an optimum concentration to maximize wicking/separation/visualization.

Coagulation of red cell upon contact with its specific antibody drastically reduces its wicking/diffusion speed on the chromatographic surface, which promotes separation of cells from the serum. This drastic reduction and differentiation of elution speeds can serve as direct indicator of the type of blood.

Example 4

Figure 4:
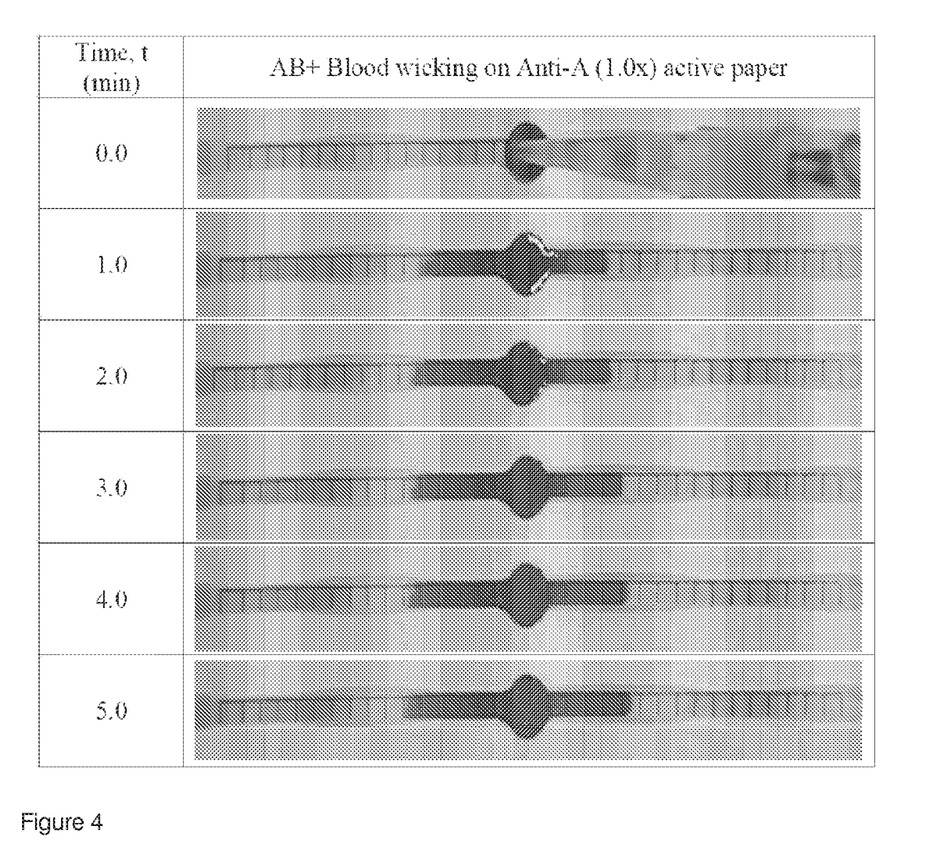
FIG. 4 is the testing device according to the present invention showing blood wicking and blood separation as a function of time.

Effect of Time on the Wicking/Separation of Blood on Bioactive Antibody Paper (see FIG. 4)

In another embodiment of the invention, the paper is first treated with specific antibodies, dried or conditioned before been exposed to a sample of pure blood. This example illustrates the effect of contact time blood-antibody treated paper on the wicking and separation performance of blood on paper.

Antibody A and B (Epiclone™ Anti-A; CSL, Australia) solutions were used. Anti-A comes as a blue colour reagent. "AB+" blood was used in this study. The blood sample was supplied into plastic vials with anti-coagulant. Paper strips (70 mm×2 mm) were made from Whatman #4 filter paper on which 2 mm unit marks were printed. Paper strips were soaked into antibody solutions (Anti-A@); phosphate buffer saline (PBS) was used as diluent. Excess antibody was removed from the paper strips with blotting papers. The antibody (Anti-A) active paper strips were then placed on Reflex Paper. Blood drops of 20 µL were dispensed at the centre of paper strip using a calibrated micro-pipette. The wicking distance was measured from centre to either direction. Pictures were taken after different intervals of time.

It can be seen that:

blood wicking/separation levels off after about 4 minutes.

There is a minimum time of contact of antibody-blood required to allow proper blood coagulation/agglutination and wicking/separation.

There is an optimum time of contact of blood-antibody-paper. Too short, the blood does not properly coagulate; too long, the separation of red cell and serum can loose some of its sharpness.

Example 5

Figure 5:
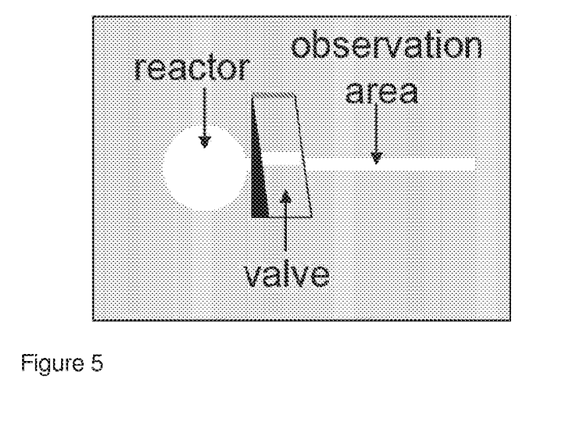
FIG. 5 shows a testing device according to the present invention incorporating a valve.

Paper Microfluidic System to Control Flow, Reaction and Dilution (see FIG. 5)

In the embodiment of the invention, paper-based microfluidic reactors can be used to conduct blood type tests. Specific antibodies are printed into the reactor designed on paper. Then blood cell suspension is introduced into the same reactor. The required period of time is allowed so that the antibodies and cell suspension can contact and mix. After a preset period of time, the valve of the reactor is closed to facilitate penetration of blood across the valve. If only the penetration of serum is observed, the test is positive because of agglutination of blood during the mixing time. If the penetration of blood is observed, the test is negative. Thus paper-based microfluidic reactor can provide a rapid visual test of blood type.

Example 6

Figure 6:
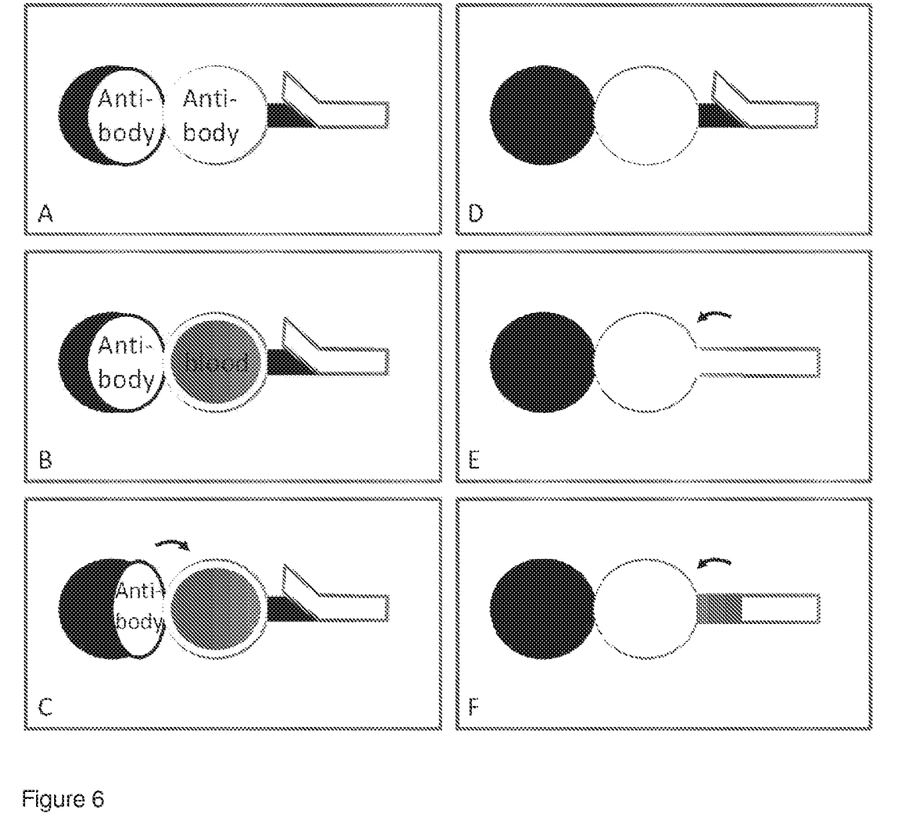

Microfluidic System with Valves (see FIG. 6)

Paper microfluidic devices can be designed to increase the ratio of blood/antibody and to provide the required time delay to allow blood and antibody interactions before the test. This example shows that all these steps can be performed using a paper device. FIG. 6 shows the design of the paper device. (A) A filter paper sheet is printed and cut as shown, and specific antibodies are either printed or deposited in the circled region. A paper switch is made on the right hand side of the device. (B) Blood sample is introduced onto the indicated region. (C) The cut paper is folded towards the blood sample as shown. (D) Blood sample is allowed to stay in contact with the antibody loaded paper for a set time. (E) After a short period of contact time, the switch is closed as shown. If the test is positive, blood will agglomerate and only serum will wick out along the switch. (F) After a short period of contact, the switch is closed as shown. If the test is negative, blood will not agglomerate and will wick out along the switch.

Example 7

Figure 7:
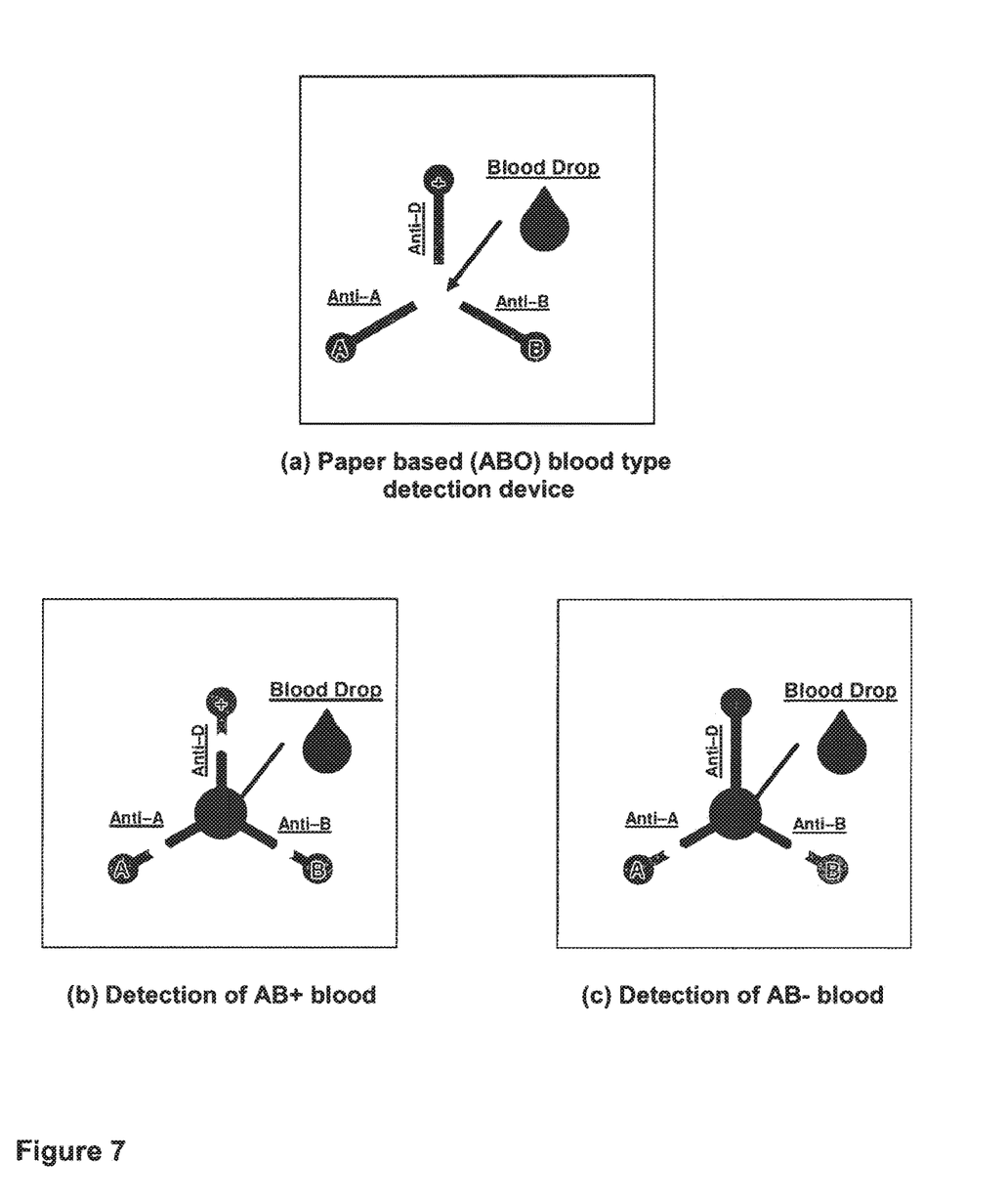
FIG. 7 are schematic representations of testing devices according to the present invention adapted for testing different blood types.

Paper microfluidic system for blood typing (See FIG. 7)

In another embodiment of the invention, a microfluidic system is printed on paper or a chromatographic medium and antibodies A, B and D (Rhesus) are printed into each of the 3 detection arms. Blood typing is analysed by placing a blood droplet in the middle reservoir and reading the results. All the different combinations of blood type and their representations are represented in FIG. 7.

Example 8

Figure 8:
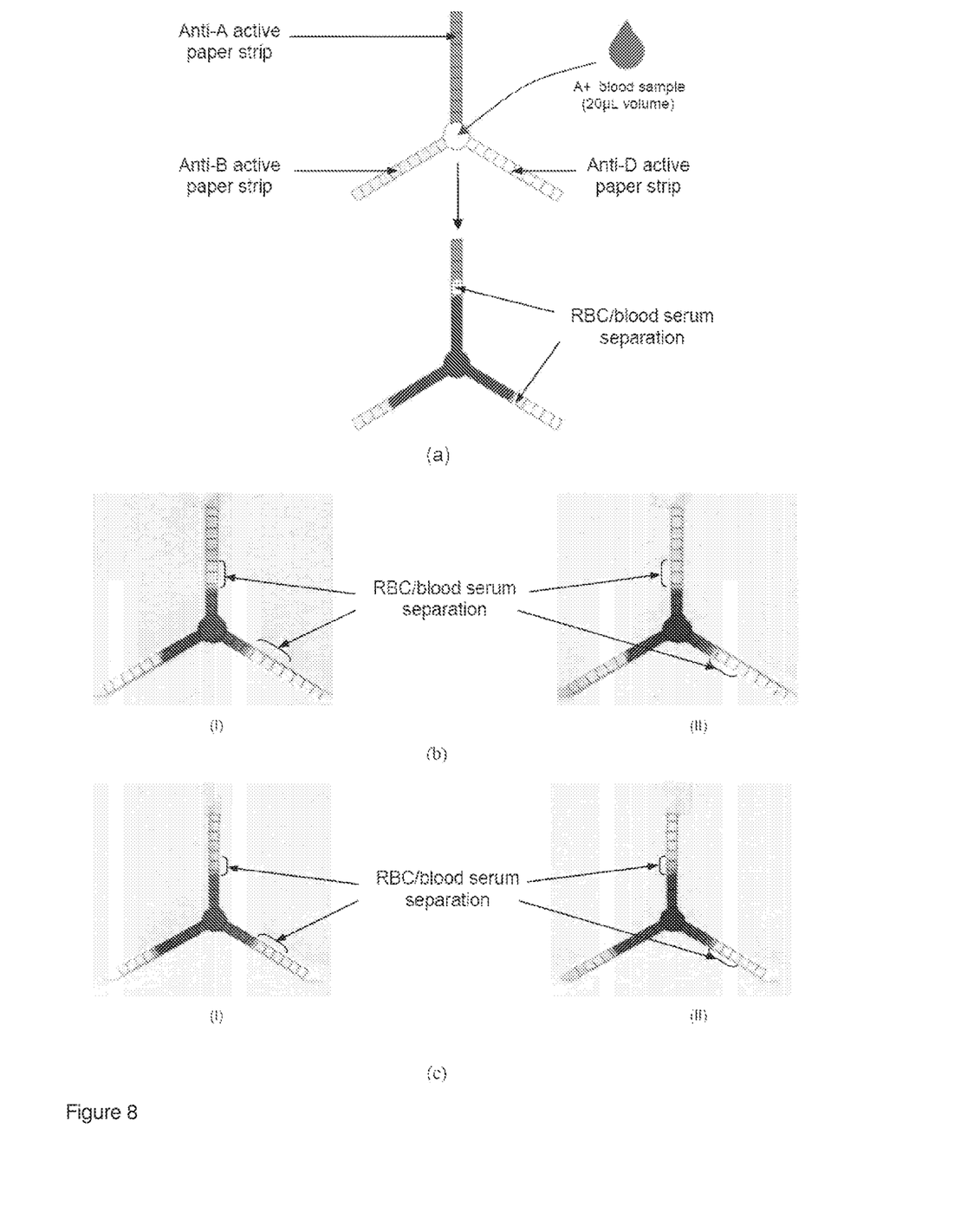
FIG. 8 shows the testing device of FIG. 7 showing the separation of red blood cells from the blood serum.

Chromatographic Separation of RBC/Blood Serum on Paper (See FIG. 8)

FIG. 8 illustrates blood group detection using chromatographic separation of red blood cells (RBC) and blood serum on antibody active paper surface; (a) schematic of chromatographic separation on paper bioassay; (b) and (c)(I) are trial 1 and 2 using A+ blood sample, respectively; (b)(II), (c)(II) are the converted images of (b)(I), (c)(I) (RGB colour to BRG colour), respectively, for better resolution.

Modifications and variations as would be deemed obvious to the person skilled in the art are included within the ambit of the present invention as claimed in the appended claims.

What is claimed:

1. A method for identifying an antigen on red blood cells of a blood sample using a single layer testing device comprising a substrate of paper material having a hydrophilic surface thereon, the surface including a collection zone and at least one detection zone extending therefrom, the detection zone having an antibody immobilized therein, the method including the steps of:

depositing the blood sample on the collection zone of the testing device;

the blood sample being transferred by capillary action to the detection zone allowing the red blood cells of the blood sample to react; and identifying the antigen on the red blood cells by a resultant visual indication arising where the antigen on the red blood cells of the blood sample reacts with an appropriate said antibody within the detection zone to thereby agglutinate the red blood cells of the blood sample, wherein the resultant visual indication results from reduced wicking and/or a differentiation of elution speeds of the blood components in the blood sample as it extends from the detection zone, due to agglutination of the red blood cells of the blood sample in the detection zone compared to wicking and/or elution speeds of the blood components of the sample as it extends from the detection zone in which antibody within the detection zone has not reacted with red blood cells of the blood sample.

2. A method according to claim 1, wherein the visual indication is due to an agglutination of the red blood cells in the blood sample upon reaction with a specific antibody resulting in reduced wicking of the red blood cells and/or separation of the red blood cells from the serum in the detection zone.

3. A method according to claim 1, including detecting blood type from the visual indication.

4. A method according to claim 1, including detecting illness from the visual indication.

* * * * *